(12) United States Patent
Garon

(10) Patent No.: US 6,223,744 B1
(45) Date of Patent: May 1, 2001

(54) WEARABLE AEROSOL DELIVERY APPARATUS

(75) Inventor: Mark Garon, Ste-Hyacinthe (CA)

(73) Assignee: Multi-Vet Ltd., Quebec (CA)

( * ) Notice: Subject to any disclaimer, the term of this patent is extended or adjusted under 35 U.S.C. 154(b) by 0 days.

(21) Appl. No.: 09/268,638

(22) Filed: Mar. 16, 1999

(51) Int. Cl.$^7$ .................................................. A61M 11/00
(52) U.S. Cl. .............................. 128/200.14; 128/200.23; 128/205.22; 128/205.23
(58) Field of Search .................. 128/200.14, 200.19, 128/200.21, 200.22, 200.23, 202.27, 202.17, 205.23, 205.11, 203.12, 203.15

(56) References Cited

U.S. PATENT DOCUMENTS

| | | | |
|---|---|---|---|
| 4,023,712 | 5/1977 | Babiak et al. | 222/175 |
| 4,061,249 | 12/1977 | Smith | 222/78 |
| 4,098,273 | 7/1978 | Glenn | 128/206 |
| 4,241,850 | 12/1980 | Speer | 222/39 |
| 4,334,531 | * 6/1982 | Reichl et al. | 128/200.14 |
| 4,446,862 | 5/1984 | Baum et al. | 128/203.15 |
| 4,524,769 | 6/1985 | Wetterlin | 128/203.15 |
| 4,972,684 | 11/1990 | Aitken | 63/8 |
| 5,020,527 | * 6/1991 | Dessertine | 128/200.23 |
| 5,027,806 | 7/1991 | Zoltan et al. | 128/200.23 |
| 5,027,808 | 7/1991 | Rich et al. | 128/203.23 |
| 5,060,643 | 10/1991 | Rich et al. | 128/200.23 |
| 5,119,806 | 6/1992 | Palson et al. | 128/200.14 |
| 5,161,524 | 11/1992 | Evans | 128/203.15 |
| 5,217,143 | 6/1993 | Aitken | 222/78 |
| 5,224,472 | 7/1993 | Pesenti et al. | 128/200.23 |
| 5,239,992 | 8/1993 | Bougamont et al. | 128/203.15 |
| 5,287,850 | 2/1994 | Haber et al. | 128/203.21 |
| 5,301,666 | 4/1994 | Lerk et al. | 128/203.15 |
| 5,347,998 | 9/1994 | Hodson et al. | 128/200.23 |
| 5,358,144 | 10/1994 | Mock | 222/78 |
| 5,404,871 | 4/1995 | Goodman et al. | 128/200.14 |
| 5,408,994 | 4/1995 | Wass et al. | 128/203.15 |
| 5,415,161 | 5/1995 | Ryder | 128/200.23 |

(List continued on next page.)

FOREIGN PATENT DOCUMENTS

| | | | |
|---|---|---|---|
| 0387222 A1 | 2/1990 | (EP) | A61M/15/00 |
| 0 587 380 | 3/1994 | (EP) . | |
| WO 90/13327 | 11/1990 | (WO) | A61M/15/00 |
| WO 90/13328 | 11/1990 | (WO) | A61M/15/00 |
| WO 97/09557 | 3/1997 | (WO) | F16K/31/06 |

OTHER PUBLICATIONS

Adrenergic Bronchodilators (Inhaled), Jun. 3, 1991, in *Consumer*.

Otto G. Raabe, The Ideal Particle Size for Optimal Pulmonary Deposition, Jun. 3, 1996, in *Advance for Respiratory Care Practitioners*.

CycloVent drawings.

*Primary Examiner*—John G. Weiss
*Assistant Examiner*—V. Srivastava
(74) *Attorney, Agent, or Firm*—Swabey Ogilvy Renault

(57) ABSTRACT

The present invention relates to a wearable aerosol delivery apparatus for releasing an aerosol with an active ingredient into an oral or nasal passage of a user. The apparatus comprises a housing comprising a first and a second surface, the first surface being adapted to be disposed against a wrist of the user, the housing defining a reservoir for containing the aerosol under pressure, an aerosol release mechanism connected with the reservoir for releasing a dose of the aerosol from the reservoir when actuated, and a fastener member attached to the housing to fasten the housing onto the user's wrist, whereby the apparatus is worn by the user and effective for delivering the active ingredient into the user's passage on demand.

17 Claims, 6 Drawing Sheets

U.S. PATENT DOCUMENTS

| | | | |
|---|---|---|---|
| 5,427,089 | 6/1995 | Kraemer | 128/200.23 |
| 5,458,135 | 10/1995 | Patton et al. | 128/200.14 |
| 5,460,171 | 10/1995 | Pesenti et al. | 128/200.23 |
| 5,474,059 | 12/1995 | Cooper | 128/200.22 |
| 5,497,764 | 3/1996 | Ritson et al. | 128/200.14 |
| 5,507,281 | 4/1996 | Kuhnel et al. | 128/203.15 |
| 5,524,613 | 6/1996 | Haber et al. | 128/203.15 |
| 5,533,505 | 7/1996 | Källstrand et al. | 128/203.15 |
| 5,564,414 * | 10/1996 | Walker et al. | 128/200.23 |
| 5,568,807 | 10/1996 | Mecikalski | 128/203.21 |
| 5,570,682 | 11/1996 | Johnson | 128/200.14 |
| 5,575,280 | 11/1996 | Gupte et al. | 128/203.15 |
| 5,575,281 | 11/1996 | Mecikalski et al. | 128/203.21 |
| 5,586,550 | 12/1996 | Ivri et al. | 128/200.16 |
| 5,610,674 | 3/1997 | Martin | 352/85 |
| 5,617,844 | 4/1997 | King | 128/200.18 |
| 5,619,984 | 4/1997 | Hodson et al. | 128/203.15 |
| 5,623,920 | 4/1997 | Bryant | 128/200.23 |
| 5,655,516 | 8/1997 | Goodman et al. | 128/200.14 |
| 5,660,169 | 8/1997 | Källstrand et al. | 128/203.15 |
| 5,676,129 | 10/1997 | Rocci, Jr. et al. | |
| 5,692,492 * | 12/1997 | Bruna et al. | 128/200.23 |
| 5,694,919 | 12/1997 | Rubsamen et al. | 128/200.14 |
| 5,718,222 | 2/1998 | Lloyd et al. | 128/200.14 |
| 5,724,962 | 3/1998 | Vidgrén et al. | 128/205.24 |
| 5,724,986 | 3/1998 | Jones, Jr. et al. | 128/725 |
| 5,730,118 | 3/1998 | Hermanson | 128/200.14 |
| 5,735,263 | 4/1998 | Rubsamen et al. | |
| 5,743,252 | 4/1998 | Rubsamen et al. | 128/200.14 |
| 5,779,122 | 7/1998 | Martinelli | 224/683 |
| 5,809,997 * | 9/1998 | Wolf | 128/200.23 |
| 5,855,307 * | 1/1999 | Biddick et al. | 128/205.22 |
| 5,899,204 * | 5/1999 | Cochran | 128/205.23 |
| 5,957,125 * | 9/1999 | Sastetter et al. | 128/200.23 |

* cited by examiner

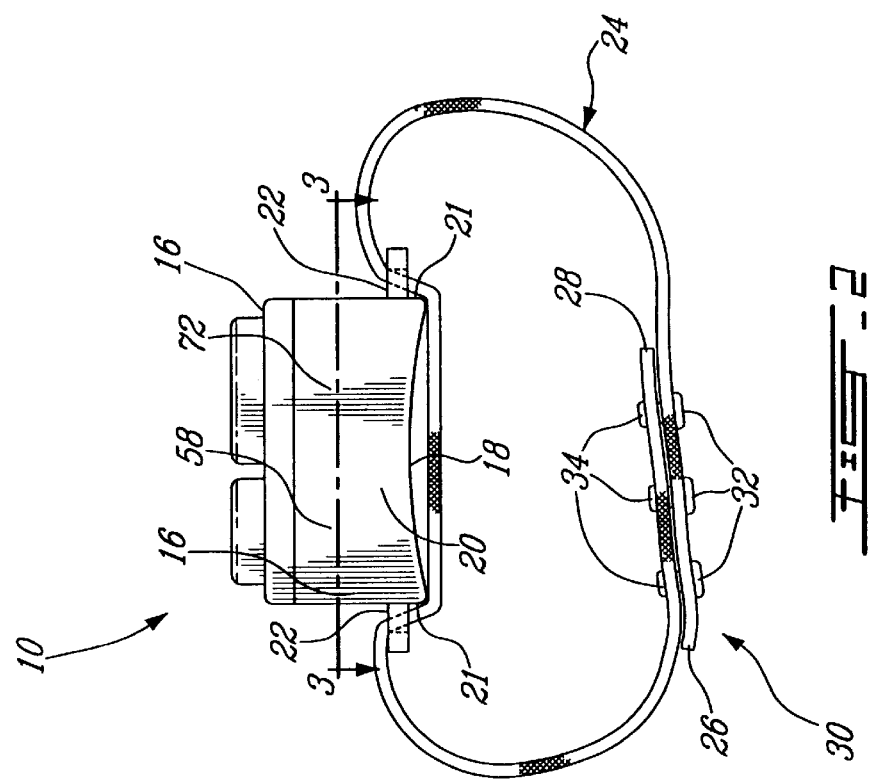
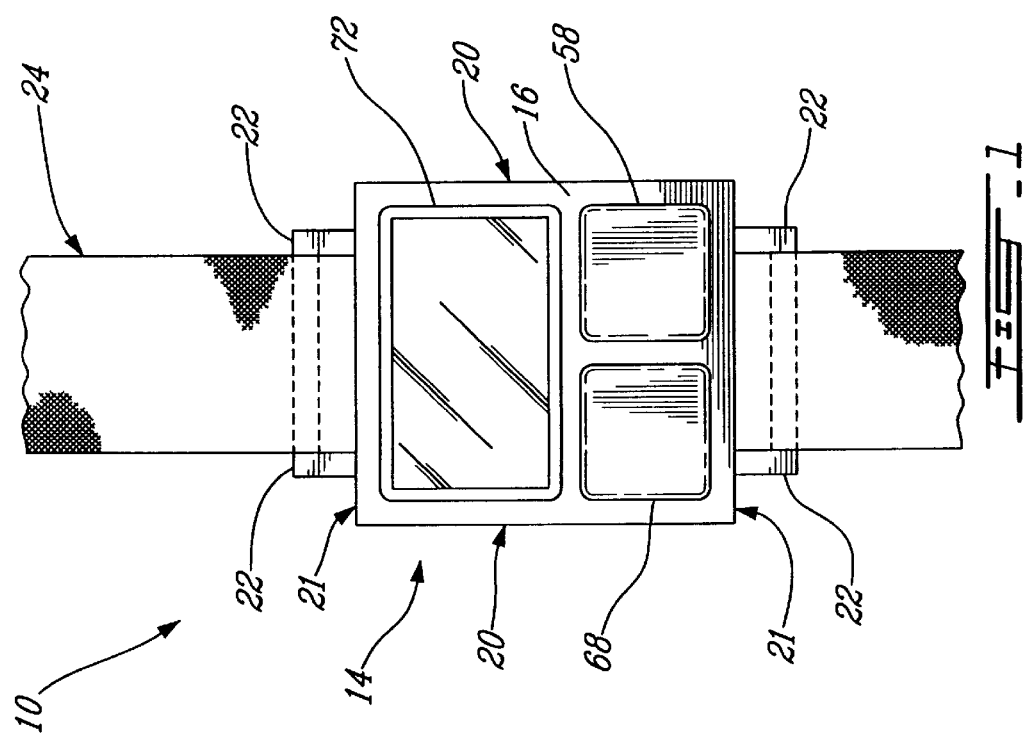

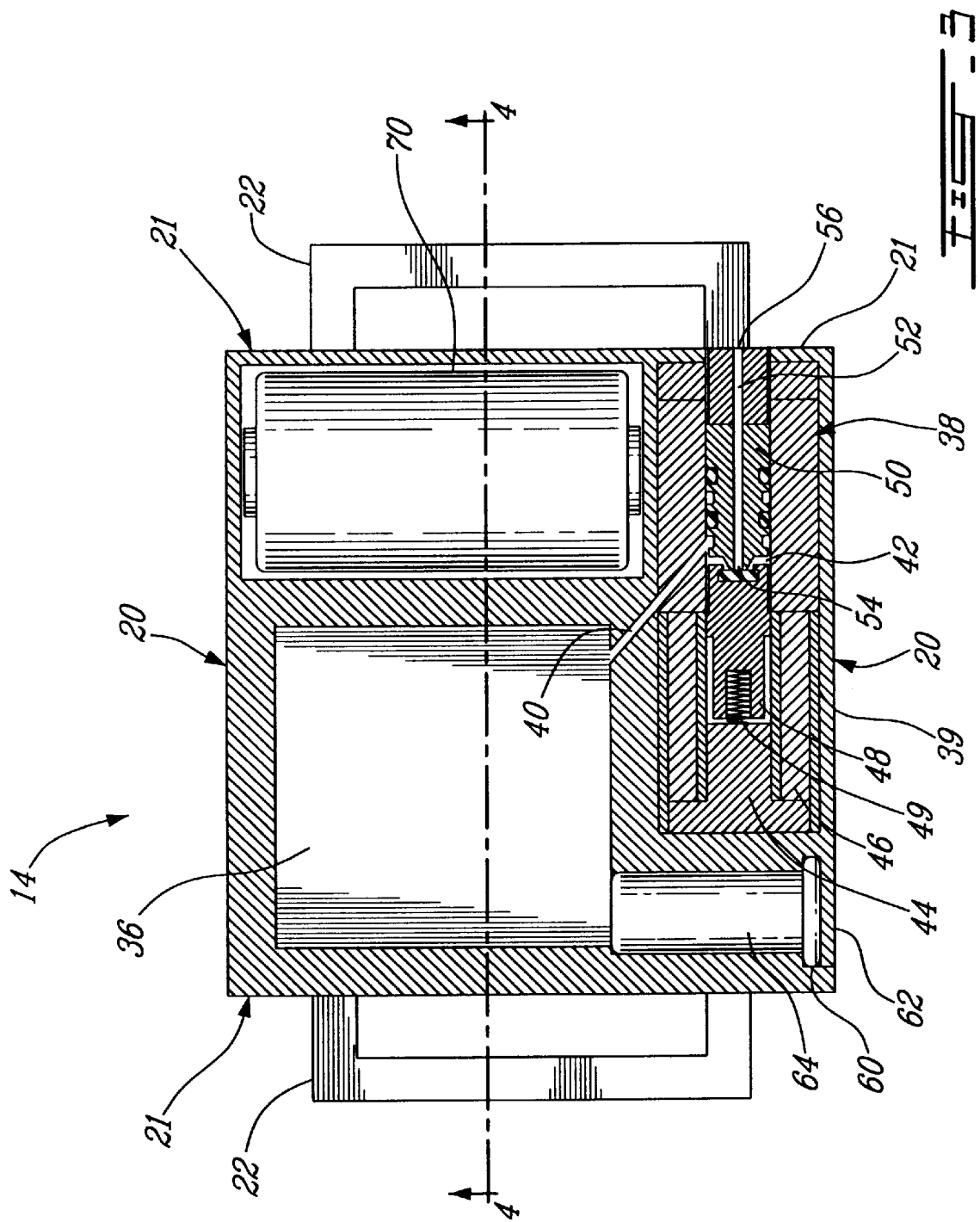

WEARABLE AEROSOL DELIVERY APPARATUS

BACKGROUND OF THE INVENTION a) Field of the Invention

The present invention relates to a portable aerosol delivery apparatus that can be worn by a user requiring a pharmaceutical treatment. The present invention particularly relates to a wearable aerosol delivery apparatus whereby a dose of a pharmacologically active agent may be readily supplied to the user.

b) Description of the Prior Art

Aerosols are used for the delivery of a variety of substances, including perfumes, repellants and drugs. Examples of drugs that may be administered in an aerosolized form include anti-convulsant, anti-arrhythmic, hormonal, anti-diuretic, corticosteroid, anti-diabetic, immune suppressive, antihistamine and anti-asthmatic agents. Asthma, for example, is a chronic inflammatory respiratory disease that may be life-threatening. Asthma affects people in varying degrees, from mild, with occasional symptoms, such as during vigorous exercise, to severe with symptoms every day. During an asthma attack, shortness of breath occurs which is caused by inflammation and bronchoconstriction. The inflammation causes the inner-lining of the airways to swell and produce excessive amounts of a thick mucus, while the bronchoconstriction causes the smooth muscle wrapped around the airways to tighten, which causes the bronchial tubes to become narrow.

Asthma may be treated with preventer or reliever agents. Preventers such as steroids are topically active agents used to control the inflammation and counter moderate and severe asthma. Relievers such as beta-agonists are bronchodilating agents that relieve bronchospasm and open the airways. Relievers are a "first-aid" treatment for asthma attacks and must be available for instant use by the patient when symptoms occur.

Compared to the oral administration, the inhaled medication goes directly to the airways and relief occurs within 5 to 10 minutes, with systemic side effects being reduced since a smaller dose is needed.

The standard apparatus for the delivery of aerosol medication is a metered-dose aerosol inhaler (MDI). A conventional MDI comprises a body having a mouthpiece covered with a cap. The body has a receptacle into which a canister is inserted. The canister contains a reservoir of medication in admixture with a pressurized propellant and a fixed-volume metered-dose chamber.

The MDI is used as follows: The user removes the cap from the mouthpiece, holds the MDI upright and shakes it. The user tilts his or her head back, breathes out, opens his or her mouth and places the mouthpiece therein. The user actuates the MDI by manually pressing the canister down into the body of the MDI as he or she simultaneously inhales for 3 to 5 seconds. Upon actuation of the MDI, a metered dose of medication is released from the reservoir, captured in the chamber and released as an aerosol mist for inhalation by the user. The user then holds his or her breath for 10 seconds to allow the medication to reach deeply into the lungs.

A first problem with conventional MDIs is that the usage technique associated therewith is complex. Coordinating the actuation of the MDI with the start of the inhalation is hard to develop and one third of children using MDIs do not have a proper MDI usage technique. Even people with a good MDI technique experience difficulties during an acute attack, when the medication is most needed. In the best conditions, only approximately 10% of the released dose is deposited into the lungs.

A second problem with conventional MDIs resides in their bulkiness. The canister generally holds over 200 doses. However, a severe asthmatic requires an average of six doses daily. Consequently, a user may be carrying daily a full month's capacity of medication. It is also difficult to determine the amount of medication remaining in the canister. Patients must calculate the number of doses taken and write the information down on a calendar, which is cumbersome. Consequently, patients rarely count the doses taken and may be carrying an empty or almost empty canister. Moreover, the pressure in the canister has a tendency to decline, reducing the effectiveness before the number of doses specified by the manufacturer has been used, which may be a cause of asthmatic exacerbation. A third problem related to the canister is that once empty, it must be thrown away and replaced. This means that in order to be safe, a user must carry an inhaler apparatus containing a canister and a "spare" canister.

Another problem with conventional MDIs is that they cannot be conveniently carried by users, for example during physical activities such as jogging, cycling and swimming or during sport competitions. In these circumstances and in others, the user may not favor carrying the MDI in a pocket or in a separate handbag. The user may have to search for the MDI during an acute attack or lose it, which may give rise to a life-threatening situation.

A fifth problem with conventional MDIs is that the parts constituting the MDI, namely the plastic inhaler, the cap and the mouthpiece must be cleaned every day to avoid a clogging buildup of medication.

There exist metered-dose inhalers that are actuated by breath. For example, reference is made to U.S. Pat. Nos. 5,404,871 and 5,655,516 issued to Goodman et al. However, such inhalers are actuated by a patient's inspiratory effort. Such inhalers detect the patient's inspiratory inhalation and release one or more pulses of aerosol medication when a pre-selected delivery threshold is exceeded, or when a new delivery threshold based on a previously detected inspiratory inhalation not exceeding the prior delivery threshold is exceeded. Other breath-actuated metered-dose inhalers release a dose when the inspiratory effort moves a mechanical lever to trigger a release valve. Such inhalers are complicated, expensive to manufacture and remain bulky.

Devices are known which allow the carrying of an asthma inhaler in a holder that may be attached to the user. For example, reference is made to U.S. Pat. No. 5,730,118 issued to Hermanson and U.S. Pat. No. 5,779,122 to Martinelli. However, such devices remain bulky and conspicuous.

Devices in the form of a bracelet or a ring that carry substances such as repellants or fragrances are known. For example, reference is made to U.S. Pat. No. 4,061,249 issued to Smith, U.S. Pat. No. 4,241,850 to Speer, U.S. Pat. Nos. 4,972,684 and 5,217,143 to Aitken and U.S. Pat. No. 5,358,144 to Mock.

It would therefore be highly desirable to provide an aerosol delivery apparatus that would be conveniently worn on a user's body at all times.

It would further be highly desirable to provide an aerosol delivery apparatus that would facilitate the usage technique.

It would further be highly desirable to provide a filling mechanism for injecting a supply of the aerosol into the reservoir.

SUMMARY OF THE INVENTION

One aim of the present invention is to provide a portable aerosol delivery apparatus that may be worn on the body of a user such as, for example, on the wrist thereof for delivering an aerosol to the user. The fact that it is conveniently secured to the user renders it readily available at all times for emergency situations, prevents loss thereof and facilitates its usage.

Another aim of the present invention is to provide a wearable aerosol delivery apparatus comprising a reservoir that may be refilled.

A further aim of the present invention is to provide a wearable aerosol delivery apparatus that may be activated by inhalation.

In accordance with one aspect of the present invention, there is provided a wearable aerosol delivery apparatus for releasing an aerosol with an active ingredient into an oral or nasal passage of a user. The apparatus comprises a housing comprising a first and a second surface, the first surface being destined to be disposed against the user's wrist, the housing defining a reservoir for containing the aerosol under pressure, an aerosol release mechanism connected with the reservoir for releasing a dose of the aerosol from the reservoir when actuated and a fastener member attached to the housing to fasten the housing onto the user's wrist, whereby the apparatus is worn by the user and effective for delivering the active ingredient into the user's passage on demand.

The apparatus may comprise a filling mechanism communicating with the reservoir for injecting a supply of the aerosol therein.

The apparatus may comprise a means for providing a signal to the user in response to a predetermined dose schedule, an indicator mounted on the housing for indicating dosage information to the user, and an indicator controller circuit connected to the indicator for receiving the signal.

The apparatus may comprise a manually activatable mechanism associated with the release mechanism for activating the release mechanism.

The apparatus may comprise a conduit associated with the release mechanism, the conduit comprising a first end mounted onto the second surface and a second end adapted to direct the aerosol into the user's passage, and a pressure sensor connected with the conduit for detecting inhalation by the user through the inhalation conduit, the pressure sensor being responsive to the detected inhalation and emitting an activation signal to actuate the release mechanism.

The apparatus may comprise an activatable locking mechanism connected to the pressure sensor, the locking mechanism comprising a movable member displaceable between a locked position and an unlocked position, the locking mechanism preventing detection by the pressure sensor when in the locked position.

In accordance with another aspect of the present invention, there is provided a method for delivering an aerosol with an active ingredient to an oral passage of a user. The method comprises the steps of providing an apparatus for releasing a dose of an aerosol from a reservoir into the user's oral passage, the apparatus being adapted to be fastened to the user's wrist, positioning the apparatus with the oral passage to direct the aerosol to the oral passage while the apparatus is fastened to the wrist, and actuating the apparatus, thereby releasing the dose into the oral passage.

The active ingredient may be released into the oral passage and may comprise a pharmacologically active agent for treating asthma.

In accordance with yet another aspect of the present invention, there is provided a method for delivering an aerosol to an oral or nasal passage of a user. The method comprises the steps of providing an apparatus for releasing an aerosol from a reservoir into the user's passage, the apparatus being adapted to be fastened to a wrist of the user, the apparatus comprising a conduit having a first end mounted to the apparatus and a second end adapted to direct the aerosol into the user's passage, positioning the conduit second end with the user's passage while the apparatus is fastened to the user's wrist, and actuating the apparatus, thereby releasing the dose into the user's passage.

The active ingredient may comprise a pharmacologically active agent for a nicotine replacement therapy.

The active ingredient may comprise an antianginal agent. The dose is more specifically released under the user's tongue.

The present invention also relates to a wearable aerosol delivery apparatus whereby a dose of a pharmacologically active agent is released into an airway of a user while the user inhales. The present invention further relates to a wearable aerosol delivery apparatus which may be activated by inhalation. In this case, coordination of the inhalation with the actuation of the apparatus is not needed.

For the purpose of the present invention the following terms are defined below.

It is to be understood that the wearable aerosol delivery apparatus of the present invention is fastenable onto a user's body part. The apparatus may be fastened onto an arm such as on a wrist or a forearm. The wearable aerosol delivery apparatus may be integrated into an adornment such as a wristwatch or a bracelet.

The term "inhalation" is intended to mean the drawing of air into the lungs such as in a nasal and/or oral inhalation.

The term "airway" is intended to mean a bronchial tube that allows the passage of air to the lungs of a user.

It is to be understood that the wearable aerosol delivery apparatus of the present invention is not limited for absorption by inhalation. Other administration routes such as lingual absorption are contemplated. Accordingly, the term "lingual" is intended to mean onto or under the tongue.

The aerosol may be released with any pharmacologically active ingredient which requires a rapid administration such as for medical emergencies and which may be administered by inhalation, lingually, through the lining of the mouth or nose, etc. Examples of pharmacologically active ingredients that may be administered in an aerosolized form include antianginal agents, agents for the treatment of asthma and other lung disorders, anti-convulsant, anti-arrhythmic, hormonal, anti-diuretic, corticosteroid, anti-diabetic, immune suppressive and antihistamine agents. Other examples include agents for nicotine replacement therapy.

The wearable aerosol delivery apparatus of the present invention may be used in conjunction with a specific pharmacologically active ingredient or with different pharmacologically active ingredient.

The speed at which the aerosol is released may be adjusted depending on the area the aerosol is to be deposited. For example, in the case of a treatment for asthma, agents are to be deposited in both large and small airways. Agents intended for systemic absorption such as peptides like insulin are to be deposited as far in the peripheral large airways of the lungs as possible.

The dose of the active ingredient may be controlled by setting the period of time during which the spray, which comprises the aerosol and the active ingredient, is released from the reservoir.

BRIEF DESCRIPTION OF THE DRAWINGS

Having thus generally described the nature of the present invention, reference will now be made to the accompanying drawings, showing by way of illustration, preferred embodiments thereof, and in which:

FIG. 1 is a top plan view of a first embodiment in accordance with the present invention;

FIG. 2 is a side elevation view of the embodiment illustrated in FIG. 1, showing the fastener member in a fastened configuration;

FIG. 3 is a top plan view of a cross-section taken

The present invention will now be described in more detail with reference to the various figures of the drawings in which like numerals refer to like components.

Figure 4:
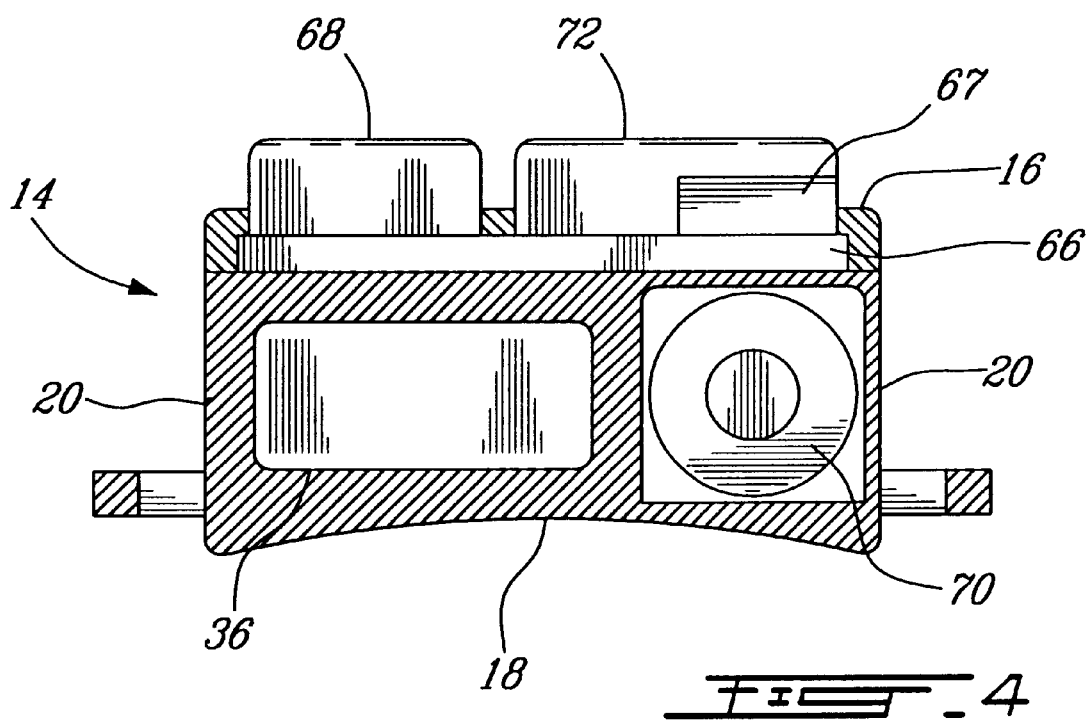
FIG. 4 is a side view of a cross-section taken along line 3—3 of FIG. 3.
Figure 5:
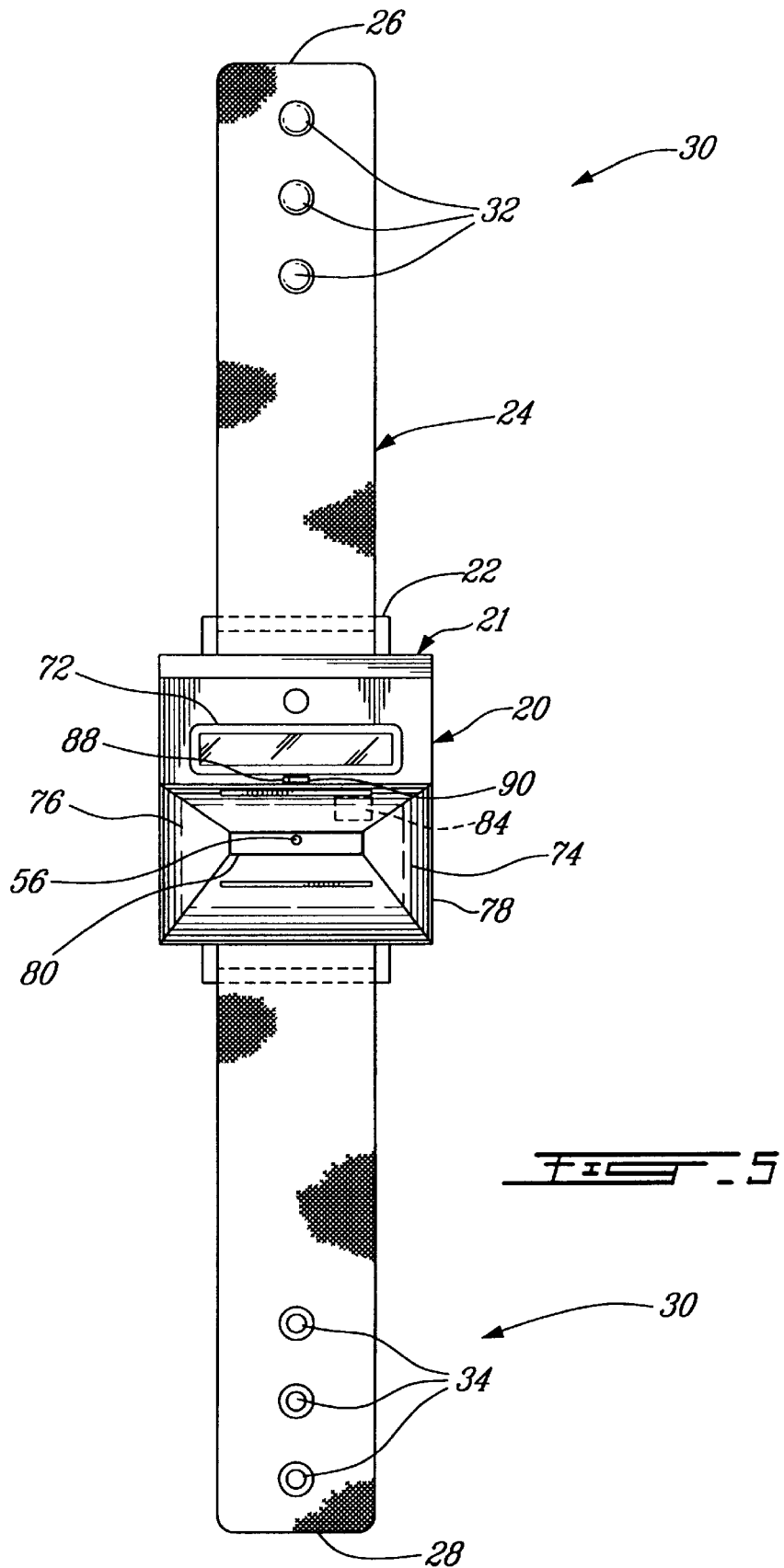
FIG. 5 is a top plan view showing another embodiment of a wearable aerosol delivery apparatus in accordance with the present invention.
Figure 6:
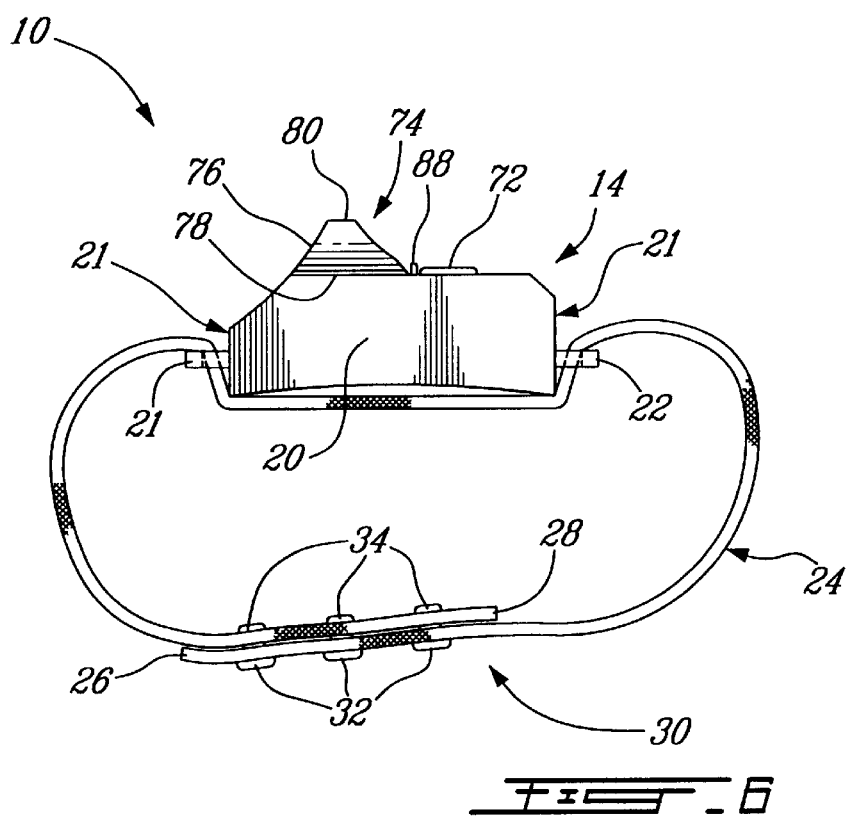
FIG. 6 is a side elevation view of the embodiment illustrated in FIG. 5.

As may be seen in FIGS. 1–4, a first embodiment of a wearable aerosol delivery apparatus 10, in accordance with the present invention, is shown herein for use with a pharmacologically active ingredient destined to a user in crisis and unable to breathe to activate the apparatus. Such an embodiment may be used for delivering a pharmacologically active agent for lingual absorption, for example.

The wearable aerosol delivery apparatus 10 comprises a housing 14. The housing 14 is configured to resemble a wristwatch casing. The housing 14 has a front surface 16, a back surface 18 opposite the front surface 16 and lateral side surfaces 20 between the front surface 16 and the back surface 18. End surfaces 21 of the housing 14 mount a pair of strap loops 22, each in the form of a U-shaped projection extending from the end surface 21 of the housing 14, respectively.

The housing 14 may be made of any suitable material that may withstand shock, for example metal or any suitable thermoplastic material such as ABS, polyethylene, polypropylene, polyamide, etc. The housing 14 may be composed of an upper casing and a lower casing, each of which may be molded, and the upper and lower casings may be welded together with an ultrasonic wielding technique.

A strap 24 of a suitable material is provided with respective ends 26 and 28. The strap 24 is threaded over the two U-shaped projections of the housing strap loops 22 of the housing 14 and under the housing back surface 18. Other watch bracelets may also be used.

The strap 24 comprises an attachment mechanism 30 for detachably fastening the wearable aerosol delivery apparatus 10 about the user's wrist. The attachment mechanism 30 comprises a series of snap elements 32 disposed on the first end 26 of the strap 24 and a series of mating socket elements 34 disposed on the second end 28 of the strap 24. The wearable aerosol delivery apparatus 10 is attached to the wrist such that the back surface 18 of the housing 14 is against the wrist and the front surface 16, the lateral side surface 20 and end surfaces 21 are exposed.

As seen in FIGS. 3–4, the housing 14 defines an aerosol reservoir 36 integral with the housing 14. The reservoir 36 may be fixed to the housing 14 by any suitable means. The reservoir 36 may be molded using a loose-core molding technique or otherwise secured to the housing 14 using an ultrasonic welding technique. The reservoir 36 may alternatively be adhered or screwed thereto. The reservoir 36 contains an aerosol under pressure. The reservoir 36 also contains a suitable inert aerosol propellant to expel the active ingredient therefrom. Such a propellant may include the DYMEL$^R$ 134*a* propellant manufactured by Dupont Fluorochemicals in Wellington, Del., USA. The reservoir 36 also contains a pharmacologically active ingredient, or a mixture of pharmacologically active ingredients, that may be aerosolized. Examples include anti-convulsant, anti-arrhythmic, hormonal, anti-diuretic, corticosteroid, anti-diabetic, immune suppressive, antihistamine and anti-asthmatic agents.

The reservoir 36 may be of any size keeping in mind its function to integrate into a housing 14 having a size which renders it wearable on the user's body. In the example shown herein, the reservoir 36 contains a limited number of doses of the aerosol with the active ingredient such as a daily number of doses. The size of the reservoir 36 is however sufficient to contain at least one dose of the aerosol with the active ingredient.

The reservoir 36 may be made of any suitable material that can resist to the pressure of the aerosol contained therein such as a rigid material like glass fiber plastic.

An aerosol release mechanism such as a solenoid valve 38 communicates with the reservoir 36 through a reservoir channel 40. The reservoir channel 40 communicates with a valve chamber 42. The valve 38 comprises a solenoid 44, which comprises a coil 46 and a plug 48, which is displaceable by way of a biased spring 49. The valve 38 comprises a valve seat 50, which defines an outlet channel 52 with a channel opening 54 at one end and a valve outlet 56 at the other end disposed through the end surface 21 of the housing 14 for releasing a predetermined dose of the aerosol from the reservoir 36. However, the valve outlet 56 may be disposed through any exposed surface of the housing 14. The plug 48 is displaceable between a closed position and an open position in response to an activation signal. When in the closed position, the plug 48 engages the valve seat 50 to close the channel opening 54 and prevent the aerosol from passing into the outlet channel 52. When in the open position (not shown), the plug 48 is at a distance from the valve seat 50 and the aerosol is able to pass into the outlet channel 52. The dose to be released is determined by setting the period of time during which the valve 38 stays in the open position. The valve 38 is kept in the open position for the period of time that the coil 46 of the valve 38 remains charged. However, the period of time during which the valve 38 may be kept in the open position may be set by the user through programming of the apparatus, or pre-programmed during the manufacturing process. Any suitable solenoid valve or other aerosol release mechanism may be used.

Referring now to FIGS. 1–2, a switch 58 actuates the valve 38. The switch 58 is disposed on the front surface 16 of the housing 14. However, the switch 58 may be disposed at any location on the housing 14, provided it may be manually pressed by the user such as by hand or against the user's teeth. Any suitable switch may be used. Examples include electronically controlled and mechanical switches.

A filling mechanism such as a second valve 60 is connected to the reservoir 36 for injecting the aerosol therein. The second valve 60 comprises a filling inlet 62 disposed through the side surface 20 of the housing 14. However, the filling inlet 62 may be disposed through any surface of the housing 14. An inlet channel 64 connects the filling inlet 62 with the reservoir 36. Examples of suitable filling valves include a one-way valve or spring-activated valve such as the 506296 lighter valve manufactured by S. T. Dupont in Paris, France.

Referring now to FIG. 4, an electronic circuit board 66 is provided in the housing 14. The circuit board 66 is connected to a microprocessor unit 67 for providing a signal to the user in response to a predetermined dose schedule programmed in the microprocessor unit 67. The microprocessor unit 67 is programmable by using a pushbutton 68 disposed on the surface of the housing 14 (FIG. 1). The microprocessor unit 67 comprises a timer mechanism such as a digital clock (not shown). Different functions such as time setting may be actuated with the pushbutton 68. Examples of microprocessor units include microchips.

A power supply such as a battery 70 (FIG. 3) is connected to the circuit board 66 for providing current to the components of the wearable aerosol delivery apparatus 10 which require energy to function such as the valve 38. The power supply may be limited to a mechanism for seating a battery in the housing 14.

An indicator such as a display 72 is mounted to the front surface 16 of the housing 14 for indicating dose schedule information to the user. Any suitable display may be used, for example a digital display such as a liquid crystal display (LCD) or a light emitting diode display (LED). Examples of information displayed include time, time of the next dose of aerosol to be administered, the number of doses remaining in the reservoir, etc.

A warning mechanism (not shown) may alternatively be used as an indicator. Any suitable warning mechanism may be used keeping in mind its function to warn the user. For example the warning mechanism may emit an audible signal such as does a piezoelectric beeper mechanism similar to that of a wristwatch, or a vibratory signal such as does a vibrator mechanism similar to that of pagers.

The wearable aerosol delivery apparatus 10 operates as follows. The user fastens the strap 24 to a wrist. When the user needs to use the apparatus 10, he or she positions the valve outlet 56 with his or her mouth while the apparatus is attached to his or her wrist. The user presses the pushbutton 68, which triggers emission of a current, which is sent through the circuit board 66 to the microprocessor unit 67. The microprocessor unit 67 causes the current to displace the valve 38 from its original closed position to its open position. A dose of the aerosol contained in the reservoir 36 is released through the valve outlet 56 of the valve 38 during a predetermined amount of time. After actuation, the valve 38 returns to the closed position.

Referring now to FIGS. 5 to 8, another embodiment of a wearable aerosol delivery apparatus 10, in accordance with the present invention.

In the embodiment shown herein, the valve 38 is actuated by an activation signal that is received upon detection of the user's inhalation, as will be described hereinafter.

A conduit 74 such as a mouthpiece or a nosepiece is connected to the front surface 16 of the housing 14 for directing the aerosol into the oral or nasal passage of the user. The conduit 74 covers the valve outlet 56 of the valve 38. The conduit 74 comprises a tubular body 76 which defines a path for the released aerosol and is adapted to direct the aerosol to the oral or nasal passage of the user when positioned therewith while the wearable aerosol delivery apparatus 10 is fastened to the user's wrist. The tubular body 76 comprises a first end 78 which is mounted to the front surface 16 of the housing 14 and a second end 80 for positioning with the user's mouth or nose. The first end 78 comprises releasably attaching means (not shown) for releasably attaching the conduit 74 to the housing 14. Examples of attaching means include threads, snap-in, etc.

The second end 80 of the conduit 74 acts as an outlet for the aerosol released from the reservoir 36.

Figure 7:
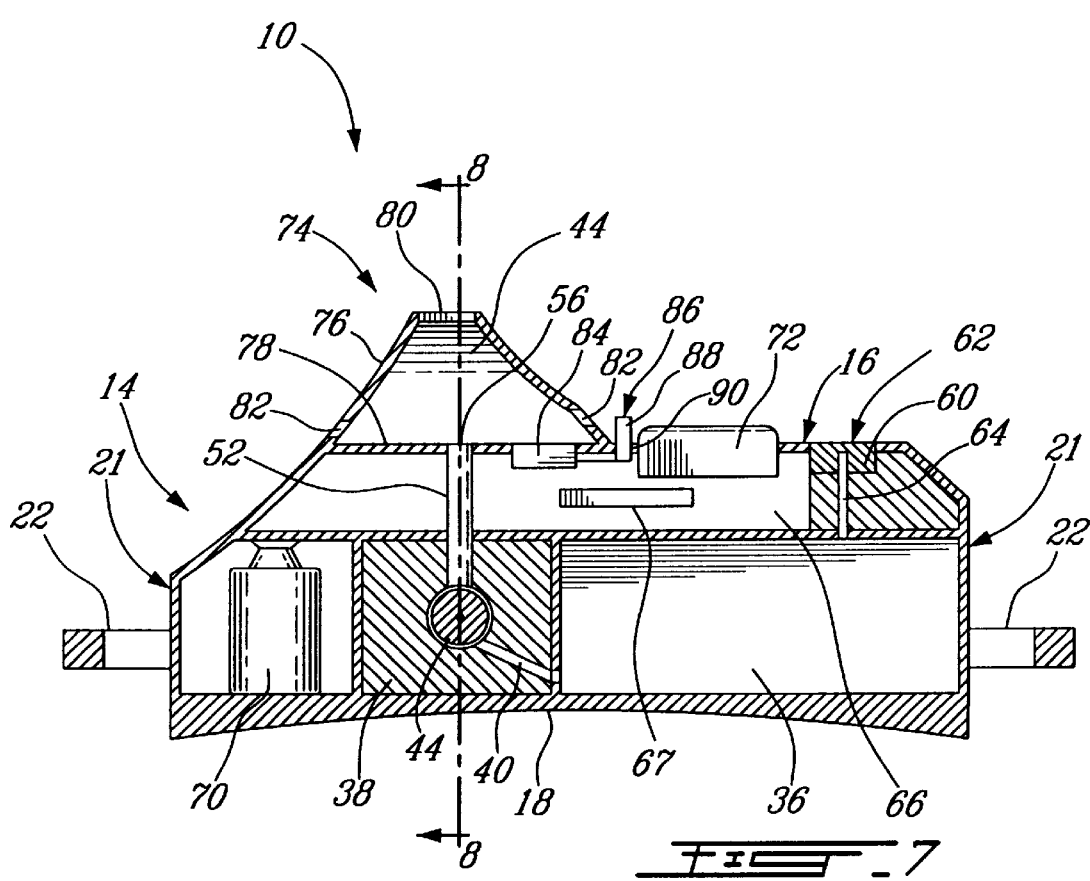
FIG. 7 is a side view of a cross-section taken along line 5—5 of FIG. 5.
Figure 8:
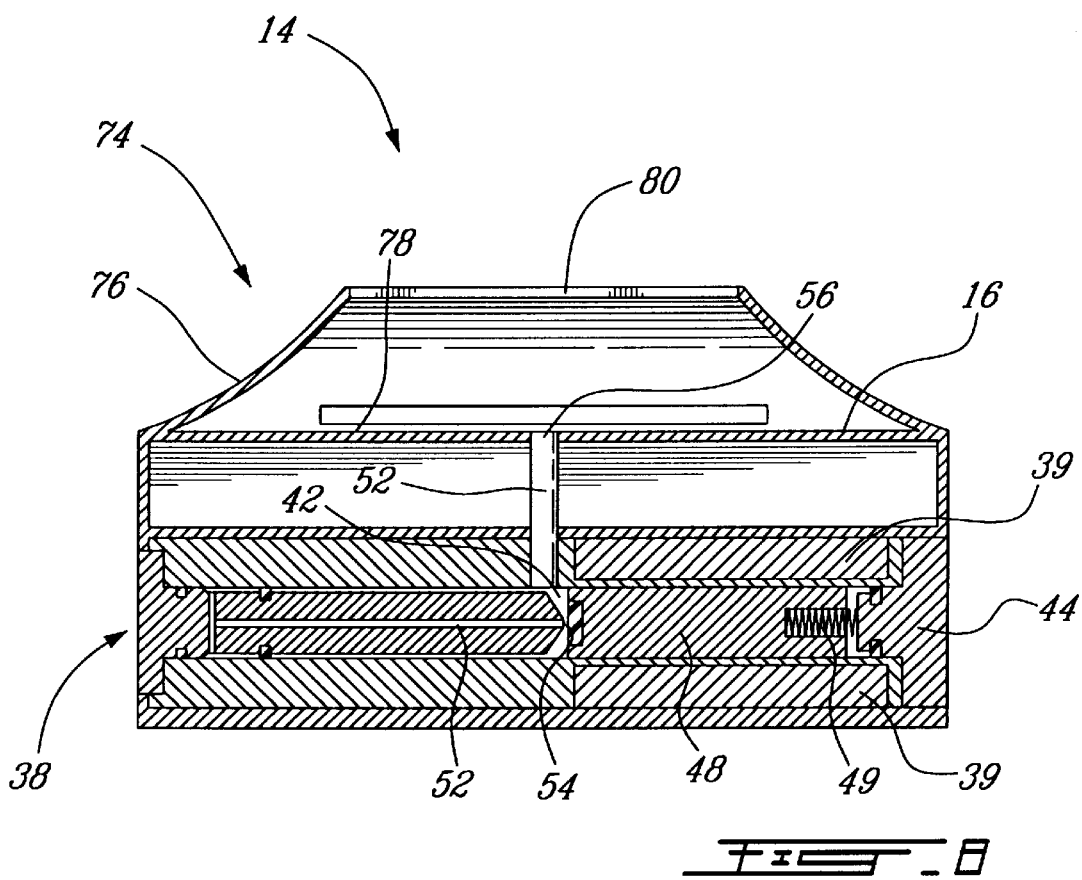
FIG. 8 is a side view of a cross-section taken along line 7—7 of FIG. 7.

Referring now to FIG. 7, the conduit 74 comprises orifices 82 that act as air inlets to enable a flow of air to be established when the user inhales therein. The conduit 74 directs the released dose of aerosol in a determined direction to the user's nose or mouth. The conduit 74 also creates a path during the user's inhalation for detection thereof and activation of the valve 38.

A pressure sensor 84 is disposed through the front surface 16 of the housing 14 and is connected with the conduit 74. The pressure sensor 84 is connected with the valve 38 with the circuit board 66. The pressure sensor 84 detects the user's inhalation through the conduit 74 by detecting air pressure differentials relative to the atmospheric pressure created in the conduit 74 as the user inhales therethrough. Upon detection of the inhalation, the pressure sensor 84 emits an activation signal to actuate the valve 38. Any suitable pressure sensor 84 may be used keeping in mind its function to emit an activation signal to the valve 38. The pressure sensor 84 may comprise a microphone such as for example the ECM60 microphone manufactured by J-Inn in Taiwan. Such a microphone detects the audio frequency of the sound of the user's inhalation and responds thereto by emitting a current to the coil of the valve 38. Upon receiving the signal, the plug is displaced and opens the valve channel connected to the reservoir, thereby releasing the predetermined dose of aerosol from the reservoir. Another example of pressure sensor 84 may be the MPXL5010 pressure sensor manufactured by Motorola, Inc. in Japan.

An actuatable lock 86 is disposed through the front surface 16 of the housing 14 and is connected to the pressure sensor 84 for preventing it from unwanted detection. The lock 86 comprises a pin 88 disposed into a slot 90 and movable manually between a locked position and an unlocked position. When the lock 86 is in the locked position, the pressure sensor 84 is prevented from detecting the inhalation of the user and triggering the aerosol release from the reservoir. The lock 86 is left in the locked position if the pressure sensor 84 needs not be used. When the lock 86 is in the second position, automatic detection of the user's inhalation is allowed. The lock 86 may be disposed on any surface of the housing 14 which may be reached by hand when the apparatus 10 is worn by the user. Any suitable lock may be used.

Figure 9:
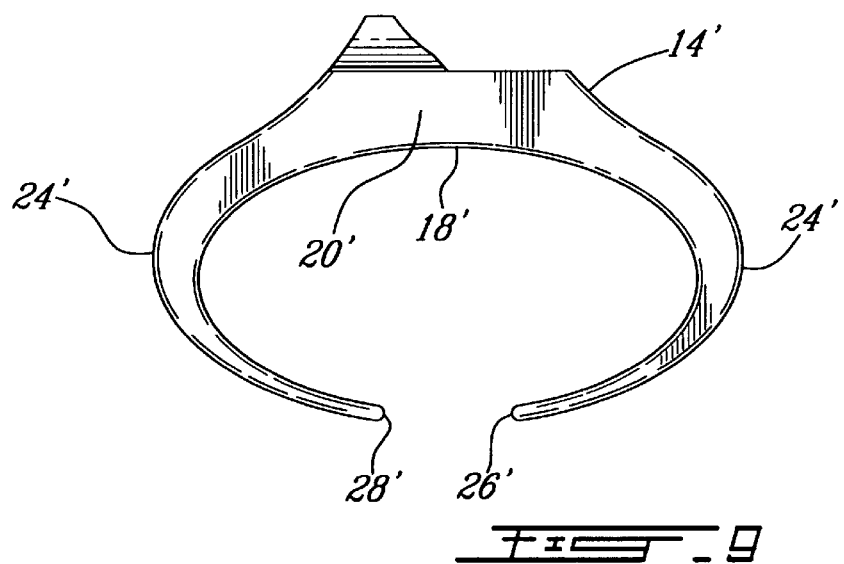
FIG. 9 is a side elevation view of yet another embodiment in accordance with the present invention.

FIG. 9 shows yet another embodiment of the wearable aerosol delivery apparatus in a form resembling that of a bracelet. The housing 14' integrates the fastener member 24'. The housing 14' is shaped to fit on the user's wrist. The reservoir (not shown) extends longitudinally beyond the front surface 16'.

The embodiments of the wearable aerosol delivery apparatus 10 shown in FIGS. 5–9 operates as follows. As mentioned above, the user fastens the strap 24 to his or her wrist. In the case where uniformity of the pharmacologically active ingredient in suspension in the aerosol is needed, the user shakes his or her wrist. The user then positions the second end 80 of the conduit 74 with his or her nose or mouth and inhales therethrough while the apparatus 10 is attached to his or her wrist. The pressure sensor 84 detects the user's inhalation. Such detection triggers emission of a current that is sent through the circuit board 66 to the microprocessor unit 67. The microprocessor unit 67 causes the current to displace the valve from its original closed position to its open position. A dose of the aerosol contained in the reservoir 36 is released through the valve outlet 56 of the valve 38 during a predetermined amount of time. The aerosol is released into the conduit 74 and reaches the airway of the user through his or her nasal or oral orifice. After actuation, the valve 38 returns to the closed position.

While the wearable inhaler apparatus in accordance with the present invention has been described, with particular reference to the illustrated embodiment, it will be understood that numerous modifications thereto will appear to those skilled in the art. Accordingly, the above description and accompanying drawings should be taken as illustrative of the invention and not in a limiting sense.

What is claimed is:

1. A small scale wearable aerosol delivery apparatus for releasing an aerosol with an active ingredient into an oral or nasal passage of a user, said apparatus comprising:
    a) a housing comprising a first and a second surface, said first surface being adapted to be disposed against a wrist of said user with the second surface substantially parallel to the first surface, said housing having a size and profile equivalent to a wristwatch;
    b) the housing defining a reservoir for containing at least one metered dose of said aerosol, with said active ingredient under pressure;
    c) an aerosol release mechanism connected with said reservoir, and contained within the housing, for releasing a dose of said aerosol from said reservoir when actuated;
    d) a fastener member attached to said housing to fasten said housing onto said user's wrist, whereby said apparatus is worn by said user and effective for delivering said at least one metered dose of aerosol containing said active ingredient into said user's passage on demand; and
    e) a filling mechanism contained within the housing and communicating with said reservoir for injecting a supply of said at least one dose of aerosol with said active ingredient into the reservoir.

2. A small scale wearable aerosol delivery apparatus according to claim 1, wherein said apparatus comprises a means for providing a signal to the user in response to a predetermined metered dose schedule, an indicator on said housing for indicating dosage information to the user; and an indicator controller circuit within said housing communicating with said indicator for receiving said signal.

3. A small scale wearable aerosol delivery apparatus according to claim 2, wherein said indicator comprises a display on said housing and wherein said indicated information is visual.

4. A small scale wearable aerosol delivery apparatus according to claim 2, wherein said indicator comprises a warning mechanism.

5. A small scale wearable aerosol delivery apparatus according to claim 4, wherein said warning mechanism comprises a piezoelectric beeper mechanism.

6. A small scale wearable aerosol delivery apparatus according to claim 4, wherein said warning mechanism comprises a vibrator mechanism.

7. A small scale wearable aerosol delivery apparatus according to claim 2, wherein said apparatus comprises a manually actuable mechanism associated with said release mechanism for activating said release mechanism.

8. A small scale wearable aerosol delivery apparatus according to claim 2, said apparatus comprising:
    a) a conduit associated with said release mechanism, said conduit comprising a first end mounted to said second surface and a second end adapted to direct said aerosol into said user's passage; and
    b) a pressure sensor connected with said conduit for detecting inhalation by said user through said conduit, said pressure sensor being responsive to said detected inhalation and emitting an activation signal to actuate said release mechanism.

9. A small scale wearable aerosol delivery apparatus according to claim 8, wherein said apparatus comprises an actuatable locking mechanism connected to said pressure sensor, said locking mechanism comprising a movable member displaceable between a locked position and an unlocked position, said locking mechanism preventing detection by said pressure sensor when in said locked position.

10. A small scale wearable aerosol delivery apparatus according to claim 8, wherein said pressure sensor comprises a microphone responsive to said user's inhalation.

11. A small scale wearable aerosol delivery apparatus according to any one of claims 7 and 10, wherein said conduit comprises a mouthpiece.

12. A small scale wearable aerosol delivery apparatus according to claim 8, wherein said conduit comprises a nosepiece.

13. A small scale wearable aerosol delivery apparatus as defined in claim 1, wherein the reservoir is of a size to contain a maximum of a daily dosage.

14. A method for delivering an aerosol with an active ingredient to an oral passage of a user, said method comprising the steps of:
    a) providing an apparatus for releasing at least one metered dose of aerosol with an active ingredient from a reservoir containing a maximum of a daily dosage into said user's passage, said apparatus being adapted to be fastened to a wrist of said user;
    b) positioning said apparatus with said oral passage to direct said aerosol to said oral passage while said apparatus is fastened to said wrist;
    c) actuating said apparatus thereby releasing said at least one metered dose into said oral passage and
    d) filling said reservoir.

15. A method according to claim 14, wherein said active ingredient comprises an antianginal agent.

16. A method according to claim 14, wherein said active ingredient is released into said oral passage, said active ingredient comprising a pharmacologically active agent for treating asthma.

17. A method according to claim 14, wherein said active ingredient comprises a pharmacologically active substance for a nicotine replacement therapy.

* * * * *